(12) United States Patent
Ogawa et al.

(10) Patent No.: US 10,155,315 B2
(45) Date of Patent: *Dec. 18, 2018

(54) MEDICAL SYSTEM AND METHOD FOR CONTROLLING THE SAME

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 222 days.

This patent is subject to a terminal disclaimer.

(21) Appl. No.: 15/000,648

(22) Filed: Jan. 19, 2016

(65) Prior Publication Data

US 2016/0135909 A1 May 19, 2016

Related U.S. Application Data

(63) Continuation of application No. PCT/JP2014/069260, filed on Jul. 18, 2014.

(30) Foreign Application Priority Data

Jul. 26, 2013 (JP) .................................. 2013-155885

(51) Int. Cl.
*B25J 9/16* (2006.01)
*B25J 3/04* (2006.01)
(Continued)

(52) U.S. Cl.
CPC ............. *B25J 9/1689* (2013.01); *A61B 34/30* (2016.02); *A61B 34/37* (2016.02); *B25J 3/04* (2013.01);
(Continued)

(58) Field of Classification Search
CPC ..... B25J 9/1689; B25J 3/04; B25J 3/00; B25J 9/0084; B25J 9/1669; A61B 34/30;
(Continued)

(56) References Cited

U.S. PATENT DOCUMENTS

2004/0039485 A1 2/2004 Niemeyer et al.
2007/0265502 A1 11/2007 Minosawa et al.
(Continued)

FOREIGN PATENT DOCUMENTS

JP 2001-087281 A 4/2001
JP 3583777 B2 11/2004
(Continued)

OTHER PUBLICATIONS

Extended Supplementary European Search Report dated Dec. 1, 2016 in related European Patent Application No. 14 82 9493.7.
(Continued)

*Primary Examiner* — Bao Long T Nguyen
(74) *Attorney, Agent, or Firm* — Scully, Scott, Murphy & Presser, P.C.

(57) ABSTRACT

There is provided a medical system that includes a multi-joint slave arm; a master arm having a joint structure structurally similar to the slave arm; and a control unit that can switch between a first control mode for controlling the rotational motion of each joint of the slave arm on the basis of the amount of rotation of each joint of the master arm so that the slave arm takes a shape similar to the master arm and a second control mode for controlling the rotational motion of each joint of the slave arm on the basis of a displacement of a predetermined region of a distal end section of the master arm so that a predetermined region of a distal end section of the slave arm follows the movement of the predetermined region of the distal end section of the master arm.

21 Claims, 14 Drawing Sheets

(51) Int. Cl.
*B25J 9/06* (2006.01)
*A61B 34/37* (2016.01)
*A61B 34/30* (2016.01)

(52) U.S. Cl.
CPC ........... *B25J 9/06* (2013.01); *A61B 2034/301* (2016.02); *Y10S 901/02* (2013.01)

(58) Field of Classification Search
CPC ......... A61B 34/32; A61B 34/37; A61B 34/74; A61B 2034/2059; A61B 2034/301; A61B 2090/067; A61B 2090/061; A61B 34/70; A61B 34/35; Y10S 901/02; Y10S 901/28; G05B 2219/40399; G05B 2219/40405; G05B 2219/40407; G05B 2219/40182
USPC .............. 700/245, 247, 250, 257; 901/2, 28; 318/568.17
See application file for complete search history.

(56) References Cited

U.S. PATENT DOCUMENTS

| | | | |
|---|---|---|---|
| 2008/0046122 A1 | 2/2008 | Manzo et al. | |
| 2012/0059519 A1 | 3/2012 | Kishi | |
| 2012/0143353 A1* | 6/2012 | Kishi | ........................ B25J 3/04 700/3 |
| 2012/0191247 A1 | 7/2012 | Kishi | |
| 2013/0110130 A1 | 5/2013 | Manzo et al. | |
| 2013/0304084 A1* | 11/2013 | Beira | .................. A61B 19/2203 606/130 |
| 2014/0121834 A1* | 5/2014 | Ogawa | ........................ B25J 3/04 700/257 |
| 2014/0171964 A1* | 6/2014 | Yang | ...................... A61B 34/30 606/130 |
| 2014/0195010 A1* | 7/2014 | Beira | ................ A61B 17/00234 700/3 |

FOREIGN PATENT DOCUMENTS

| | | |
|---|---|---|
| JP | 2005-131417 A | 5/2005 |
| JP | 2006-167867 A | 6/2006 |
| JP | 4176126 B2 | 11/2008 |
| JP | 2009-539573 A | 11/2009 |
| JP | 4608601 B2 | 1/2011 |
| JP | 2012-055996 A | 3/2012 |
| JP | 2012-148379 A | 8/2012 |
| JP | 2013-022651 A | 2/2013 |
| WO | WO 2007/146987 A2 | 12/2007 |
| WO | WO 2013/012018 A1 | 1/2013 |

OTHER PUBLICATIONS

International Search Report dated Aug. 26, 2014 issued in PCT/JP2014/069260.

* cited by examiner

MEDICAL SYSTEM AND METHOD FOR CONTROLLING THE SAME

CROSS-REFERENCE TO RELATED APPLICATIONS

This is a continuation of International Application PCT/JP2014/069260, with an international filing date of Jul. 18, 2014, which is hereby incorporated by reference herein in its entirety. This application claims the benefit of Japanese Patent Application No. 2013-155885, filed on Jul. 26, 2013, the content of which is incorporated herein by reference.

TECHNICAL FIELD

The present invention relates to a medical system and a method for controlling the same.

BACKGROUND ART

As an operation input apparatus for remotely operating a slave arm having a joint, in the related art there is a known medical system provided with a master arm having a joint structure similar to the joint structure of the slave arm is known (e.g., refer to Patent Literatures PTL 1 and PTL 2 below). In such a system, because the slave arm can be made to reproduce a motion corresponding to the motion of the master arm, an operator can intuitively operate the slave arm while directly recognizing the shape and motion of the slave arm from the shape and motion of the master arm.

During an actual surgical operation, it is necessary to move the slave arm not only minutely but also by a comparatively great amount when, for example, pulling an affected area or tying a knot after hooking a needle. In this case, because an operator needs to pay attention to the positional relationship between the slave arm and peripheral tissues inside the body of the patient, he or she wishes to accurately perceive the shape and orientation of the entire slave arm, including the joint part. Meanwhile, when performing intricate treatment of, for example, the affected area, it is necessary to accurately move a distal end of the slave arm provided with a distal treatment part. In this case, the operator wishes to focus attention only on the operation of the distal end of the slave arm without paying attention to the overall shape or orientation of the slave arm.

On the other hand, scale conversion techniques between a master and a slave that differ in structure are generally well known (e.g., refer to Patent Literature PTL 3). In contrast, for a master and a slave that are similar in structure, such as for the system of Patent Literatures PTL 1 and PTL 2, the ratio of the amount of motion of the slave arm to the amount of operation of the master arm (motion scale ratio) is uniquely determined according to the structure ratio between the master arm and the slave arm, and it may not be possible to change the operating condition of the slave arm, depending on the circumstances.

CITATION LIST

Patent Literature

PTL 1

Publication of Japanese Patent No. 3583777

PTL 2

Publication of Japanese Patent No. 4608601

PTL 3

Publication of Japanese Patent No. 4176126

SUMMARY OF INVENTION

A first aspect of the present invention is a medical system including: a multi-joint slave arm; a master arm that has a joint structure structurally similar to the slave arm and is operated by an operator; and a control unit that controls the slave arm on the basis of an operation applied to the master arm, wherein the control unit can switch between a first control mode for controlling a rotational motion of each joint of the slave arm on the basis of an amount of rotation of each joint of the master arm so that the slave arm takes a shape similar to the master arm and a second control mode for controlling the rotational motion of each joint of the slave arm on the basis of a displacement of a predetermined region of a distal end section of the master arm so that a predetermined region of a distal end section of the slave arm follows a movement of the predetermined region of the distal end section of the master arm.

A second aspect of the present invention is a method for controlling a medical system including a multi-joint slave arm and a master arm that has a joint structure structurally similar to the slave arm and that is operated by an operator, wherein a control mode for controlling the slave arm can be switched between a first control mode for controlling a rotational motion of each joint of the slave arm on the basis of an amount of rotation of each joint of the master arm so that the slave arm takes a shape similar to the master arm and a second control mode for controlling a rotational motion of each joint of the slave arm on the basis of a displacement of a predetermined region of a distal end section of the master arm so that a predetermined region of a distal end section of the slave arm follows a movement of the predetermined region of the distal end section of the master arm.

DESCRIPTION OF EMBODIMENTS

First Embodiment

A medical system 100 according to a first embodiment of the present invention will now be described with reference to the drawings.

Figure 1:
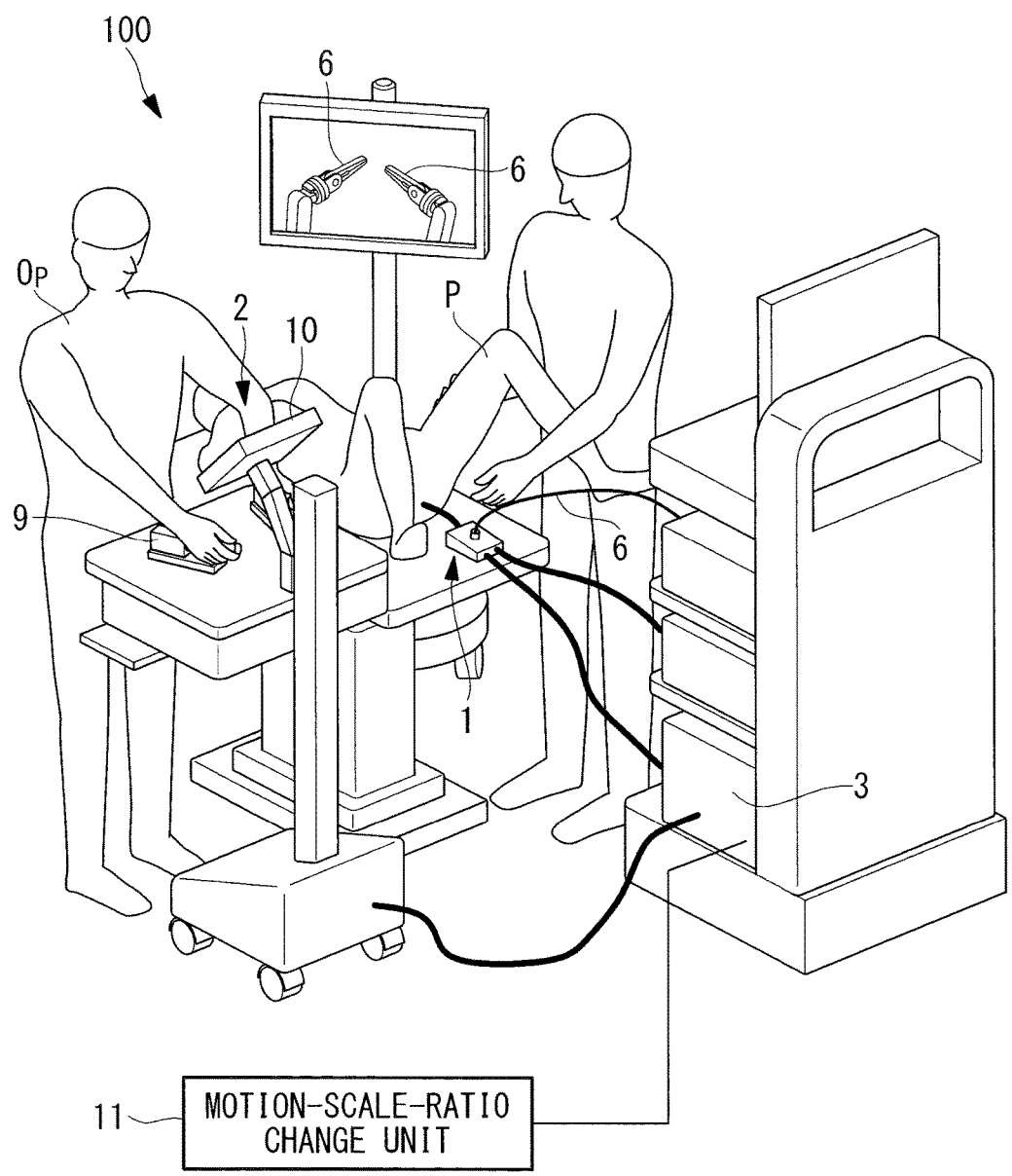
FIG. 1 is a block diagram depicting the overall structure of a medical system according to a first embodiment of the present invention.

As shown in FIG. 1, the medical system 100 of this embodiment includes a manipulator 1 that is inserted into the body of a patient P, as well as an operation input unit 2 and a control unit 3 that are disposed surrounding an operating table on which the patient P lies.

First of all, the outline of the medical system 100 will be described. An endoscope 5 and slave arms 6, as described below, are provided at a distal end of the manipulator 1. When an operator Op inserts the manipulator 1 into the body of the patient P via the anus and operates the operation input unit 2 while observing an intracorporeal image acquired by the endoscope 5, on a display unit 10 provided at the operation input unit 2, the control unit 3 controls the manipulator 1 on the basis of the operation applied to the operation input unit 2. By doing so, the operator Op remotely operates the manipulator 1 positioned in the body and can administer treatment to the inside of the body by means of the slave arms 6 provided in the manipulator 1.

Each structure of the medical system 100 will now be described.

Figure 2:
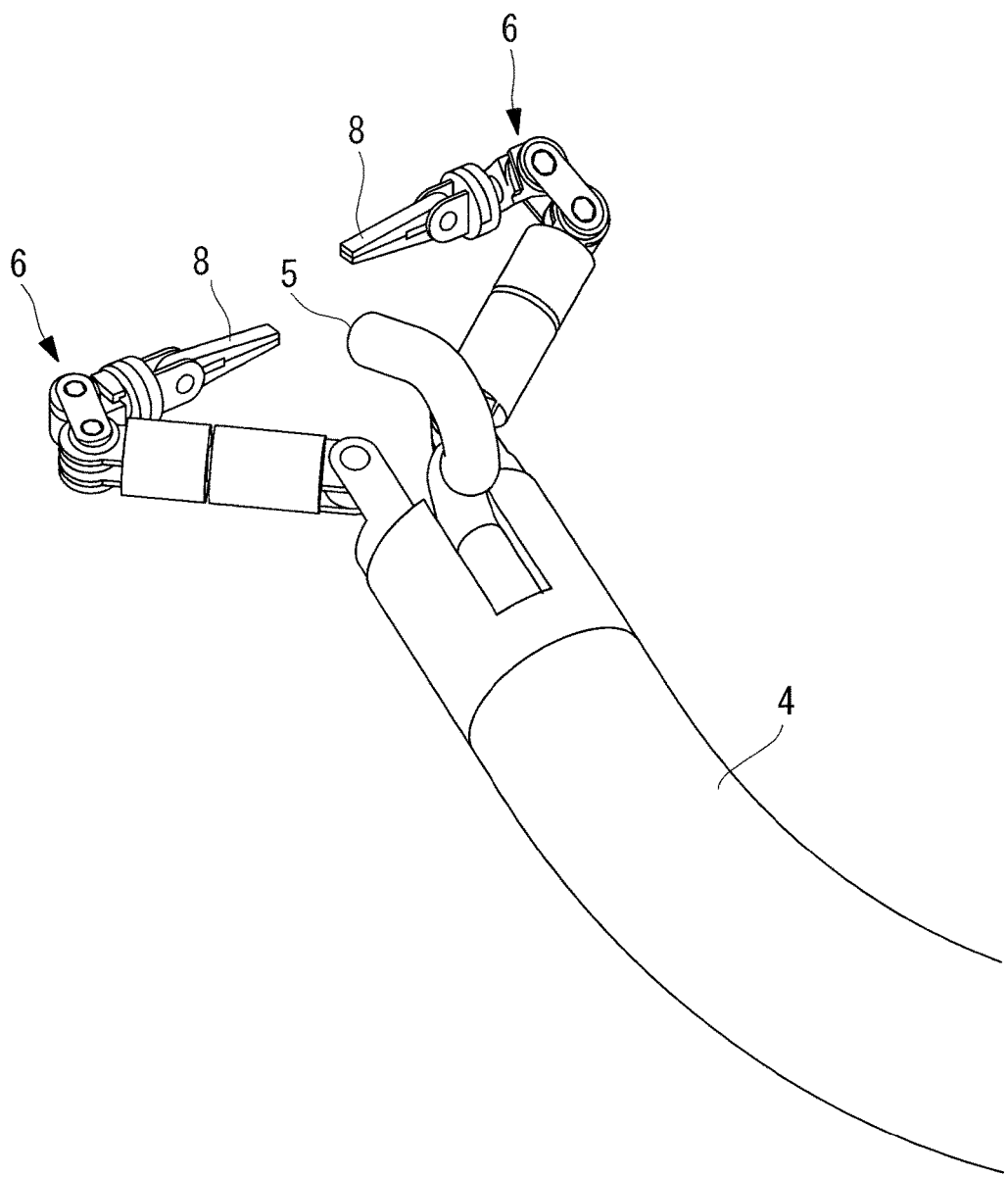
FIG. 2 is an outside view depicting the structure of a distal portion of a manipulator provided in the medical system in FIG. 1.

As shown in FIG. 2, the manipulator 1 includes an elongated flexible part 4 that is inserted into the body and the endoscope 5 and the slave arms 6 provided at a distal end of the flexible part 4. Although FIGS. 1 and 2 show a two-armed manipulator 1 having two slave arms 6, the manipulator 1 may be single-armed, having a single slave arm 6, or may have three or more slave arms 6.

The slave arms 6 have a plurality of joints and, at the distal end thereof, are provided with a treatment part 8 such as a forceps or an electrocauter.

The operation input unit 2 includes master arms 9 operated by the operator Op and the display unit 10. A master arm 9 is provided for each of the slave arms 6.

Figure 3:
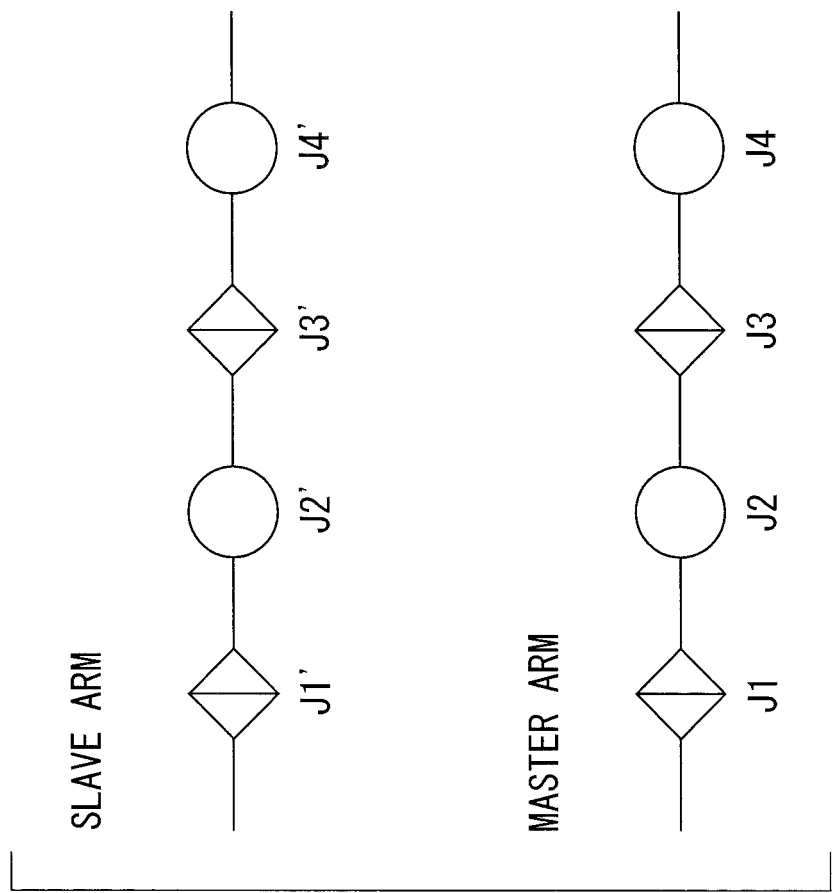
FIG. 3 is a diagram schematically depicting joint structures of a slave arm and a master arm provided in the medical system in FIG. 1.

FIG. 3 schematically shows joint structures of a slave arm 6 and a master arm 9. As shown in FIG. 3, the master arm 9 has a joint structure similar to that of the slave arm 6. In the present example, the slave arm 6 includes a roll joint J1', a yaw joint J2', a roll joint J3', and a yaw joint J4' in that order from the basal end. Likewise, the master arm 9 includes a roll joint J1, a yaw joint J2, a roll joint J3, and a yaw joint J4 in that order from the basal end. The roll joints J1', J3', J1, and J3 rotate about a roll axis extending in the longitudinal direction of the arms 6 and 9 from the base to the distal end of each of the arms 6 and 9, and the yaw joints J2', J4', J2, and J4 rotate about a yaw axis orthogonal to the roll axis (orthogonal to the drawing of FIG. 3). In addition, the ratios of the distances between contiguous joints of both the arms 6 and 9 are identical.

Each joint Ji (i=1, 2, 3, 4) of the master arm 9 is provided with an angle detector, such as an encoder. The operation input unit 2 detects the amount of change θi (i=1, 2, 3, 4) in the angle of each joint Ji with the angle detector and outputs the detected four amounts of change θi to the control unit 3 as operation signals.

The control unit 3 generates a drive signal for driving each joint Ji' (i=1, 2, 3, 4) of the slave arm 6 on the basis of the operation signals received from the operation input unit 2 and transmits the generated drive signal to the manipulator 1. The manipulator 1 rotates each joint Ji' by means of a control signal to move the slave arm 6.

The medical system 100 of this embodiment further includes a motion-scale-ratio change unit (motion-ratio change unit) 11. The motion-scale-ratio change unit 11 is provided, for example, at the operation input unit 2, so that the operator Op can set an arbitrary value as a motion scale ratio. Here, the motion scale ratio is defined by the following expression, as described in detail below.

Motion scale ratio=(displacement of slave arm)/(displacement of master arm)

The motion-scale-ratio change unit 11 may be provided so as to be capable of switching the motion scale ratio in a step-by-step manner between the scale ratio established by a structure ratio between the master arm 9 and the slave arm 6 and a predetermined value smaller than that scale ratio.

The motion scale ratio selected by the motion-scale-ratio change unit 11 is transmitted to the control unit 3. The control unit 3 switches a control mode for controlling the slave arm 6 between a "first control mode" and a "second control mode" on the basis of the received motion scale ratio.

A method for controlling the slave arm 6 by this control unit 3 will now be described in detail.

Figure 4:
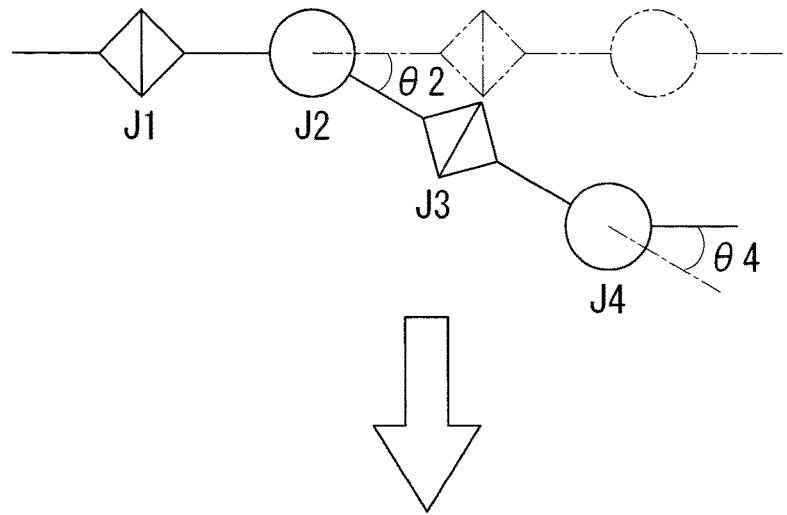
FIG. 4 is a diagram for explaining an operation in a first control mode of the slave arm in FIG. 3.
Figure 4:
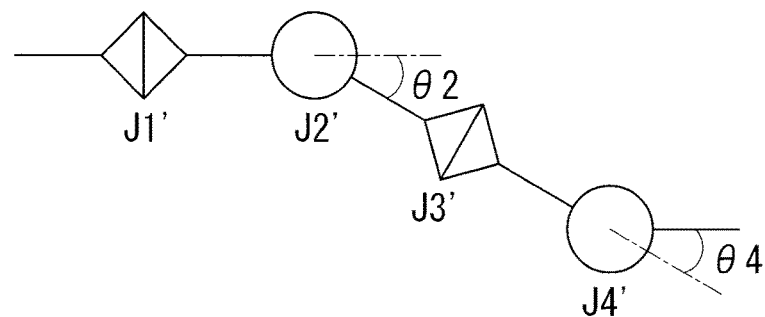

The "first control mode" is a mode in which the entire slave arm 6 is made to follow the overall motion of the master arm 9. More specifically, as shown in FIG. 4, the control unit 3 rotates each joint Ji' of the slave arm 6 by the amount equal to the amount of change θi in each joint Ji of the master arm 9. At this time, the ratio between the amount of operation applied to the master arm 9 and the amount of motion of the slave arm 6 (motion scale ratio) is the structure ratio between the master arm 9 and the slave arm 6. This structure ratio is set in the motion-scale-ratio change unit 11 as a default ratio for the motion scale ratio.

The "second control mode" is a mode that is selected by the control unit 3 when the received motion scale ratio is below the aforementioned default ratio structurally established in the first control mode and is a mode in which the distal end of the slave arm 6 is made to follow the motion of the distal end of the master arm 9.

Figure 5:
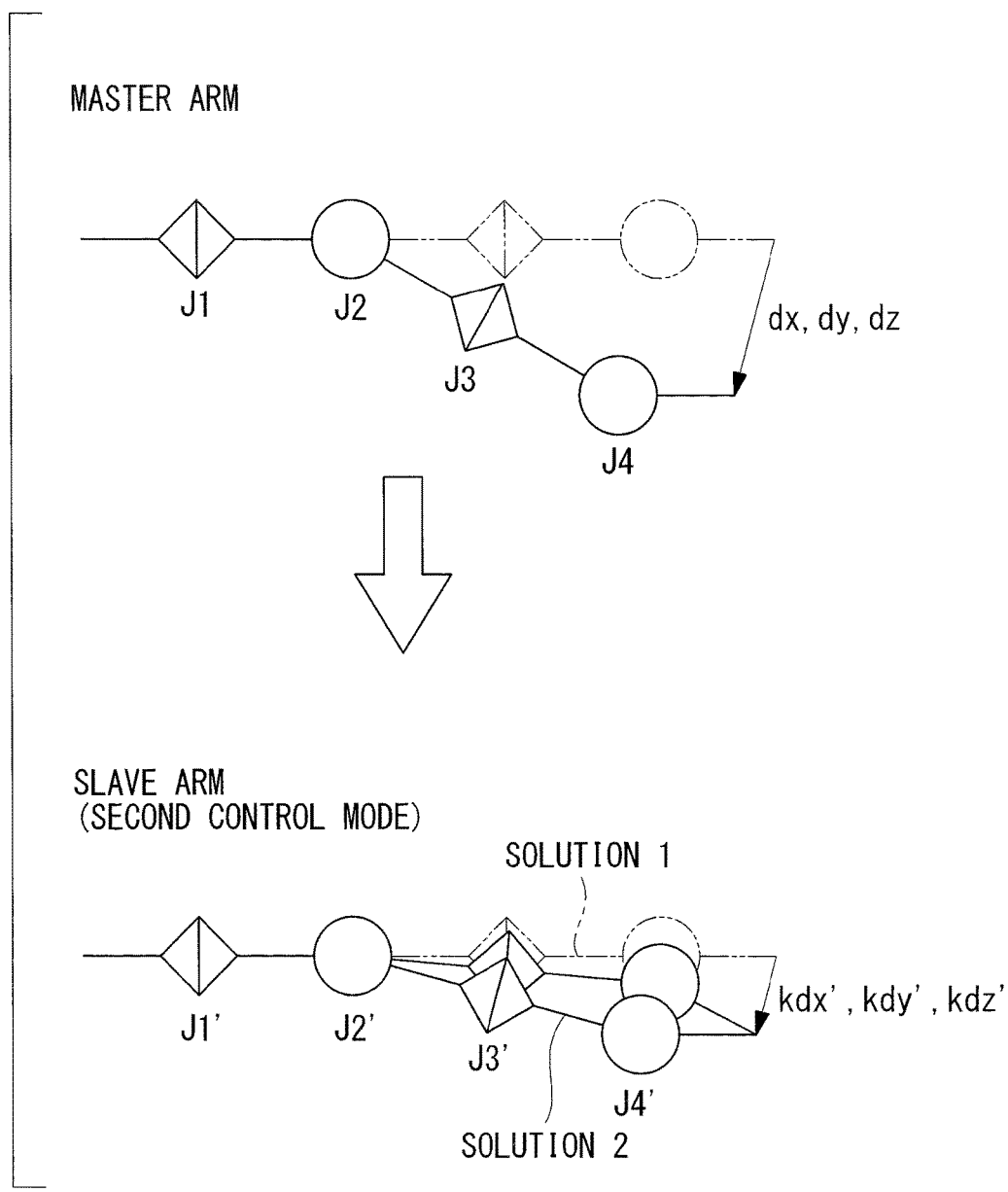
FIG. 5 is a diagram for explaining an operation in a second control mode of the slave arm in FIG. 3.

More specifically, the control unit 3 calculates forward kinematics of the master arm 9 using the amount of change θi in each joint Ji received from the operation input unit 2, thereby calculating displacements dx, dy, dz of the distal end of the master arm 9 in each direction of the motion coordinate system for the master arm 9, as shown in FIG. 5. Next, the control unit 3 converts the obtained displacements dx, dy, dz into the displacements dx', dy', dz' in each direction of the operating coordinate system for the slave arm 6. Then, the control unit 3 calculates reverse kinematics of the slave arm 6 on the basis of the obtained displacements dx', dy', dz' to obtain the amount of rotation θi' in each joint Ji' of the slave arm 6 as a solution, thereby rotating each joint Ji' by the obtained amount of rotation θi'.

It is desirable that the displacements dx', dy', dz' be converted into displacements after having been converted into the coordinate system of the display unit 10 so that the motion direction of the slave arm 6 displayed on the display unit 10 coincides with the operating direction of the master arm 9.

Here, the control unit 3 multiplies the displacements dx', dy', dz' by the motion scale ratio k and uses the obtained displacements kdx', kdy', kdz' for calculating the reverse kinematics. This motion scale ratio k is a motion scale ratio set by the operator Op in the motion-scale-ratio change unit 11.

Although the distal end of the slave arm 6 controlled in this "second control mode" moves in a direction corresponding to the movement direction of the distal end of the master arm 9, the displacement thereof is reduced relative to the displacement of the distal end of the master arm 9. If the motion scale ratio is set, for example, to "0.2," the displacement of the distal end of the slave arm 6 is one-fifth of the displacement of the master arm 9.

Here, in reverse kinematics, because two or more combinations of the amounts of rotation θi' are possible for moving the distal end of the slave arm 6 by displacements kdx', kdy', kdz', as shown in FIG. 5, two or more solutions to reverse kinematics are possible, accordingly. FIG. 5 shows, for example, two solutions (solution 1, solution 2). If a plurality of solutions are obtained, the control unit 3 adopts the solution that causes the overall shape of the slave arm 6 to be closest to the overall shape of the master arm 9 (solution 2 in the example of FIG. 5), for example, the solution that minimizes the total of differences between rotational angles of the corresponding joints Ji and Ji'.

Next, the operation of the medical system 100 with the aforementioned structure will now be described with reference to FIGS. 6 through 8.

In order to administer treatment to the inside of the body of the patient P using the medical system 100 of this embodiment, the flexible part 4 of the manipulator 1 is inserted into the body of the patient P, and the distal end of the manipulator 1 is moved close to an affected area while a video image of the inside of the body acquired by the endoscope 5 is being observed on the display unit 10. Next, while observing the video image displayed on the display unit 10, the operator Op operates the master arm 9 to move the slave arm 6 and administers, to the affected area or a peripheral area thereof, for example, pre-treatment required for treatment of the affected area.

Figure 6:
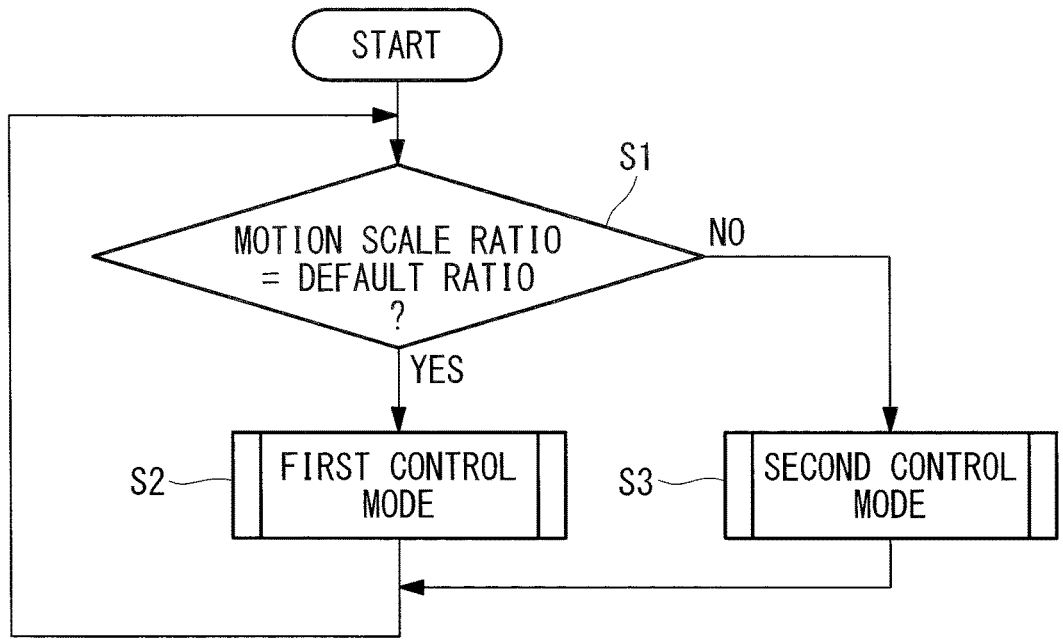
FIG. 6 is a flowchart illustrating a method for controlling the manipulator with a control unit of the medical system in FIG. 1.

At this time, the operator Op normally causes the slave arm 6 to move in the "first control mode" by means of the motion-scale-ratio change unit 11 (YES in step S1), as shown in FIG. 6 (step S2).

Figure 7:
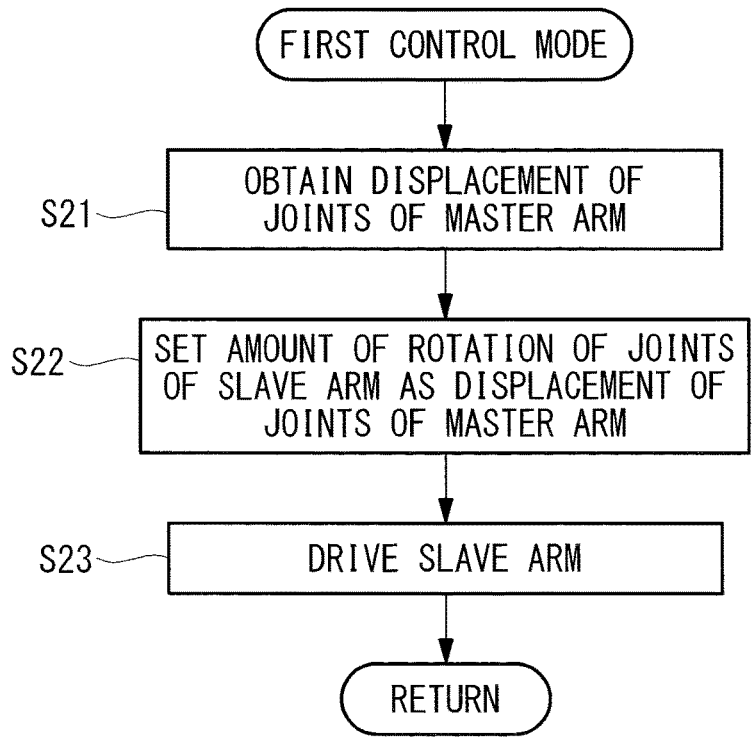
FIG. 7 is a flowchart illustrating a routine for the first control mode in FIG. 6.

As shown in FIG. 7, in the "first control mode," each joint Ji' of the slave arm 6 is rotated by the amount equal to the amount of change θi in each joint Ji of the master arm 9 (steps S21, S22), and consequently, the entire slave arm 6 follows the motion of the entire master arm 9 (step S23). In other words, because the shape and orientation of the entire master arm 9 correspond to the shape and orientation of the entire slave arm 6, the operator Op can directly recognize the current shape and orientation of the slave arm 6 from the master arm 9. For this reason, while operating the slave arm 6 in a narrow lumen, the operator Op can properly operate the slave arm 6, while paying attention to the overall shape of the slave arm 6, for example, checking to see if a cubital part (joints J2, J4) of the slave arm 6 compresses the intraluminal wall.

Next, for the treatment of the affected area, the operator Op positions the treatment part 8 close to the affected area and then causes the motion-scale-ratio change unit 11 to set the motion scale ratio as a value smaller than the default ratio established in the "first control mode," for example, to "0.2" (NO in step S1). By doing so, the slave arm 6 becomes controlled in the "second control mode" (step S3).

Figure 8:
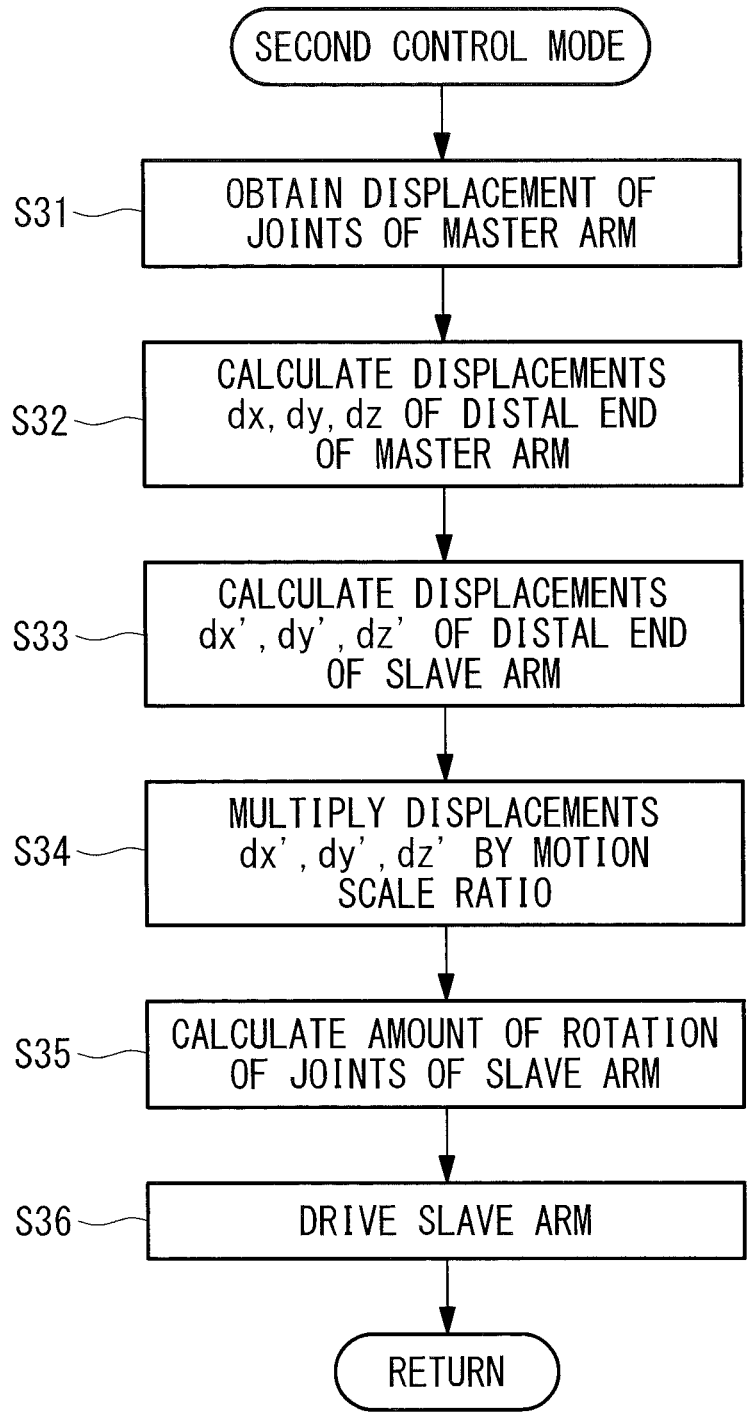
FIG. 8 is a flowchart illustrating a routine for the second control mode in FIG. 6.

As shown in FIG. 8, in the "second control mode," the slave arm 6 is controlled (step S36) so that the distal end of the slave arm 6 follows the motion of the distal end of the master arm 9 (steps S33, S35), on the basis of the movement of the distal end of the master arm 9 (steps S31, S32). The amount of motion of the distal end of the slave arm 6 at this time is one-fifth of the amount of operation of the distal end of the master arm 9 (step S34), thus micro-moving the distal end of the slave arm 6 at low speed. Therefore, the operator Op can easily realize minute motion of the treatment part 8 at the distal end of the slave arm 6 and can accurately administer intricate treatment by means of the treatment part 8.

Furthermore, in the "second control mode," as long as the distal end of the slave arm 6 is moved within a restricted range of the affected area and surroundings thereof, the entire slave arm 6 can be prevented from moving by a great amount. As a result, the operator Op can focus attention only on the operation of the distal end of the slave arm 6 without having to pay attention to the overall shape of the slave arm 6. Furthermore, when a plurality of solutions are obtained as a result of calculating the reverse kinematics in step S33, a solution that gives a shape close to a right master arm 11R is selected, and the overall shape and orientation of the slave arm 6 roughly correspond to the overall shape and orientation of the master arm 9. Therefore, the operator Op can coarsely recognize the shape and orientation of the slave arm 6 from the master arm 9.

In this manner, this embodiment affords an advantage in that the motion scale ratio is changed between a situation requiring a large motion and a situation requiring a minute motion of the slave arm 6, so that the slave arm 6 is allowed to move under a condition appropriate for each of the situations, thereby enhancing usability.

Although, in this embodiment, the slave arm 6 is driven with a motion scale ratio equal to or smaller than the motion scale ratio determined by the structure ratio between both arms 6 and 9, it may be possible that the slave arm 6 is driven with a motion scale ratio greater than the above-described structure ratio.

By doing so, the motion scale ratio can be set as a value larger than the above-described structure ratio to allow the entire slave arm 6 to move by a greater amount, which is useful, for example, for coarse treatment of a wide area.

Furthermore, in this embodiment, when the "second control mode" is switched to the "first control mode," it is preferable that the control unit 3 perform a reset flow before the "first control mode" is started. In the reset flow, the control unit 3 moves at least one of the slave arm 6 and the master arm 9 to allow the positions and the orientations of both arms 6 and 9 to correspond to each other.

Instead of automatically executing the above-described reset flow by the control unit 3, it may be performed manually by allowing the operator Op to operate the master arm 9. In this case, because it is difficult to achieve a perfect match between the positions and the orientations of both arms 6 and 9, the control unit 3 may end the reset flow when the shifts of the rotational angles between corresponding joints Ji, Ji' of both arms 6 and 9 fall within a predetermined range. Furthermore, in this case, the control unit 3 may display on the display unit 10 an indication for prompting the operator Op to operate the master arm 9.

Although, in this embodiment, the solution that causes the overall shapes of both arms 6 and 9 to be closest to each other is adopted if a plurality of solutions are obtained as a result of calculating the reverse kinematics, the method for selecting a solution is not limited to this.

For example, a solution with which the positions of the most distal corresponding joints J4, J4' are matched may be selected. In this case, because the orientation of the treatment part 8 corresponds to the orientation of the distal portion of the master arm 9, the operator Op can operate the treatment part 8 more intuitively.

Figure 9:
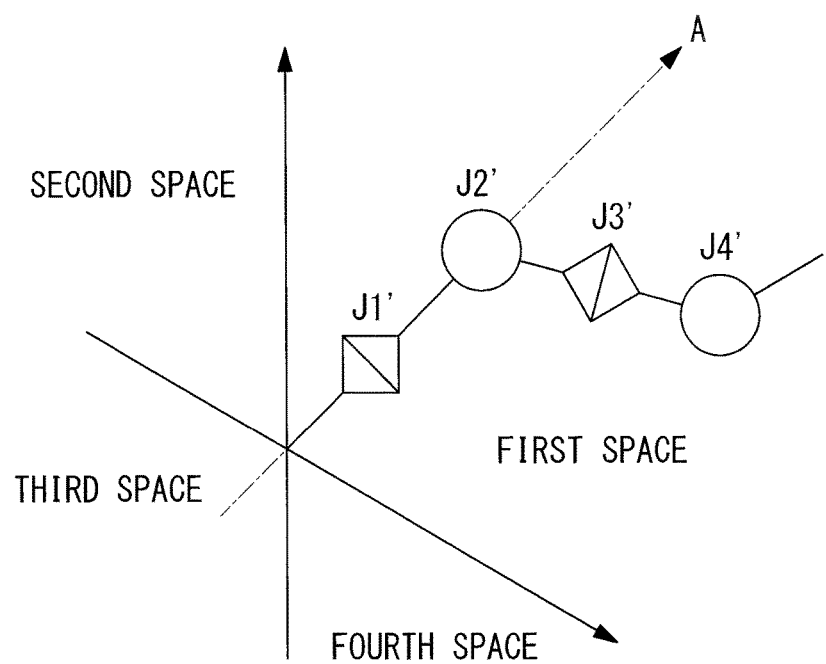
FIG. 9 is a diagram for explaining a modification of a method for selecting a solution to reverse kinematics.

Alternatively, from among first through fourth spaces as shown in FIG. 9, a solution that ensures that the slave arm 6 is located in the quadrant identical to that in which the master arm 9 is located may be adopted. The first through fourth spaces are four spaces that are obtained by defining a central axis A of a basal part of each of the arms 6 and 9 and that are divided by two planes that pass through the axis A and are orthogonal to each other. In this case, the overall orientation of the slave arm 6 can be made to correspond to the overall orientation of the master arm 9.

Second Embodiment

A medical system 200 according to a second embodiment of the present invention will now be described with reference to FIGS. 10 through 16.

Figure 10:
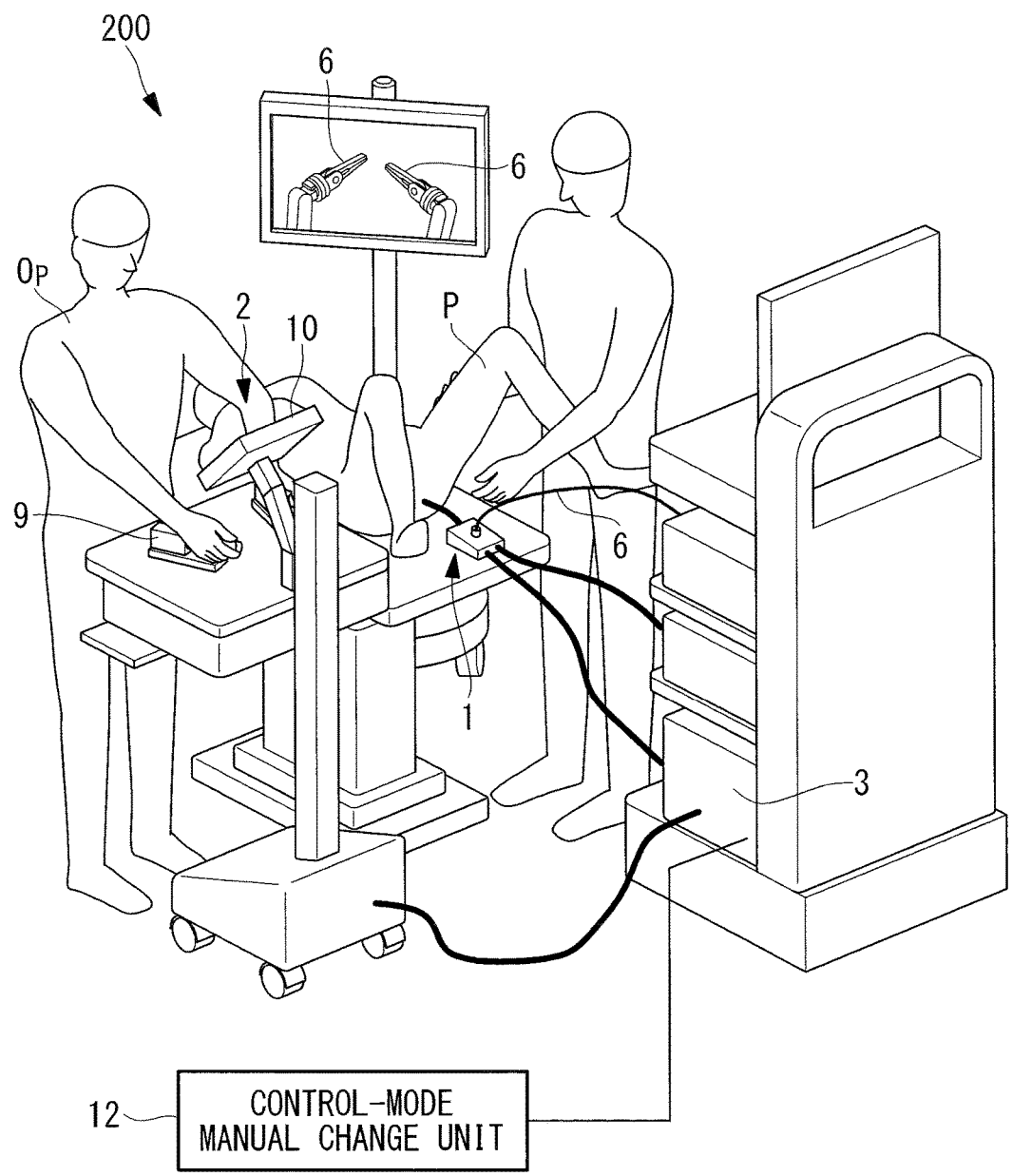
FIG. 10 is a block diagram depicting the overall structure of a medical system according to a second embodiment of the present invention.

As shown in FIG. 10, the medical system 200 according to this embodiment differs from that in the first embodiment mainly in that a control-mode manual change unit 12 is provided and in the "second control mode." For this reason, in this embodiment, the control-mode manual change unit 12 and the "second control mode" will mainly be described, and structures in common with those in the first embodiment will be denoted with the same reference signs, and descriptions thereof will be omitted.

Figure 11:
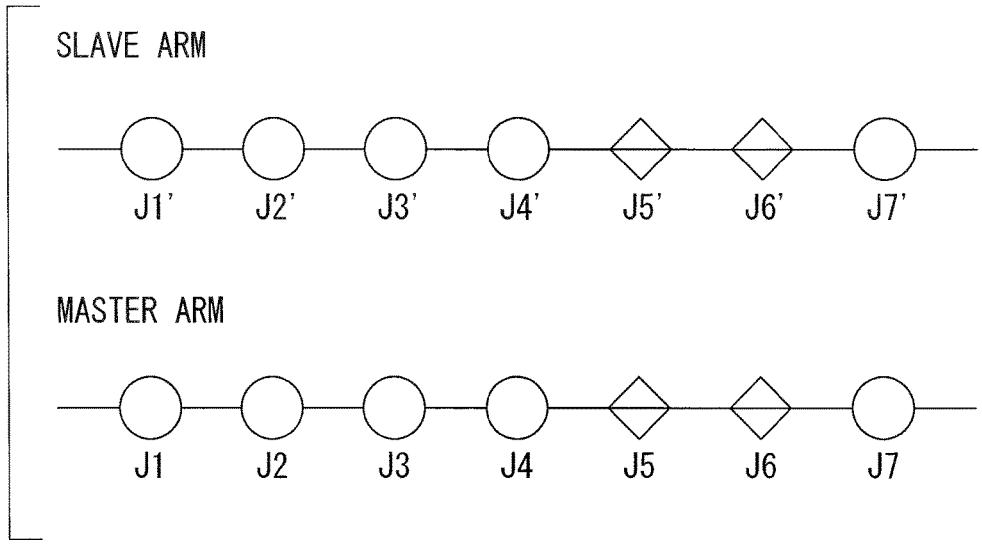
FIG. 11 is a diagram schematically depicting a joint structure of a slave arm and a master arm provided in the medical system in FIG. 10.

In this embodiment, as shown in FIG. 11, the slave arm 6 and the master arm 9 having comparatively many (seven in the present example) joints Ji', Ji (i=1, 2, . . . , 7) will be described. Also in this embodiment, the slave arm 6 and the master arm 9 have a joint structure similar to each other. In this embodiment, the slave arm 6 and the master arm 9 having a comparatively small number of joints, as described in the first embodiment, may also be used.

The control-mode manual change unit 12 is provided, for example, at the operation input unit 2 such that one of the "first control mode" and the "second control mode" can be selected by the operator Op. A signal indicating the control mode selected by the control-mode manual change unit 12 is transmitted to the control unit 3, which then controls the slave arm 6 in the control mode specified by the received signal.

Figure 12:
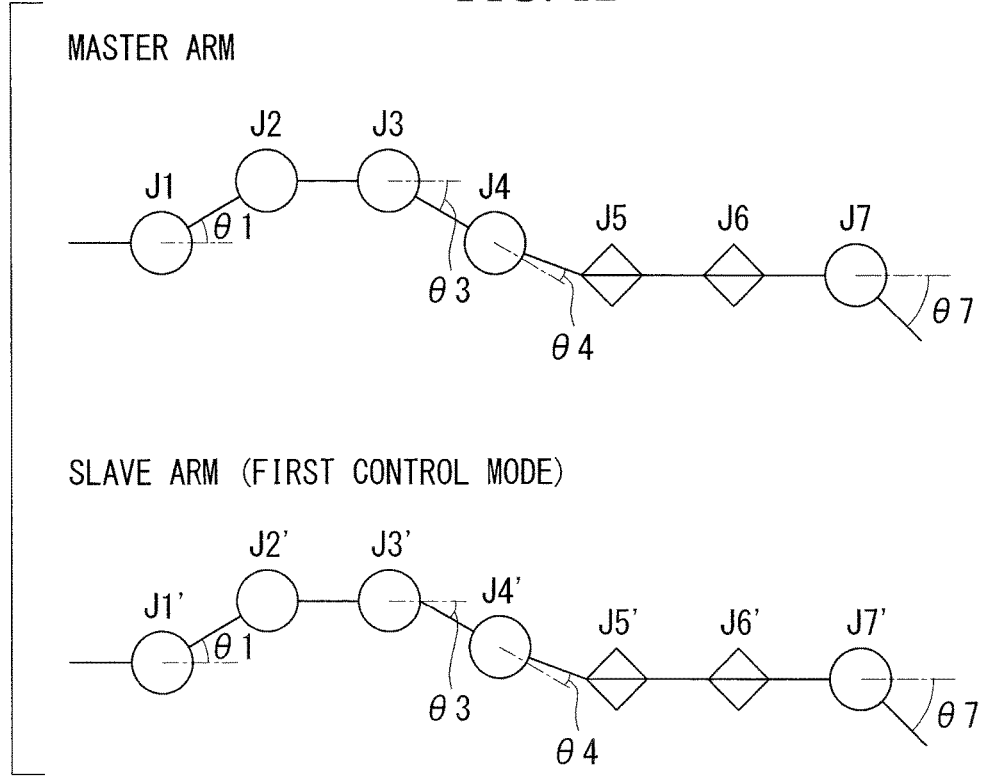
FIG. 12 is a diagram for explaining an operation in a first control mode of the slave arm in FIG. 11.

Next, a method for controlling the slave arm 6 by this control unit 3 will be described in detail. As shown in FIG. 12, the "first control mode" is the same as the "first control mode" described in the first embodiment, except in the number of joints, and descriptions thereof will be omitted.

Figure 13:
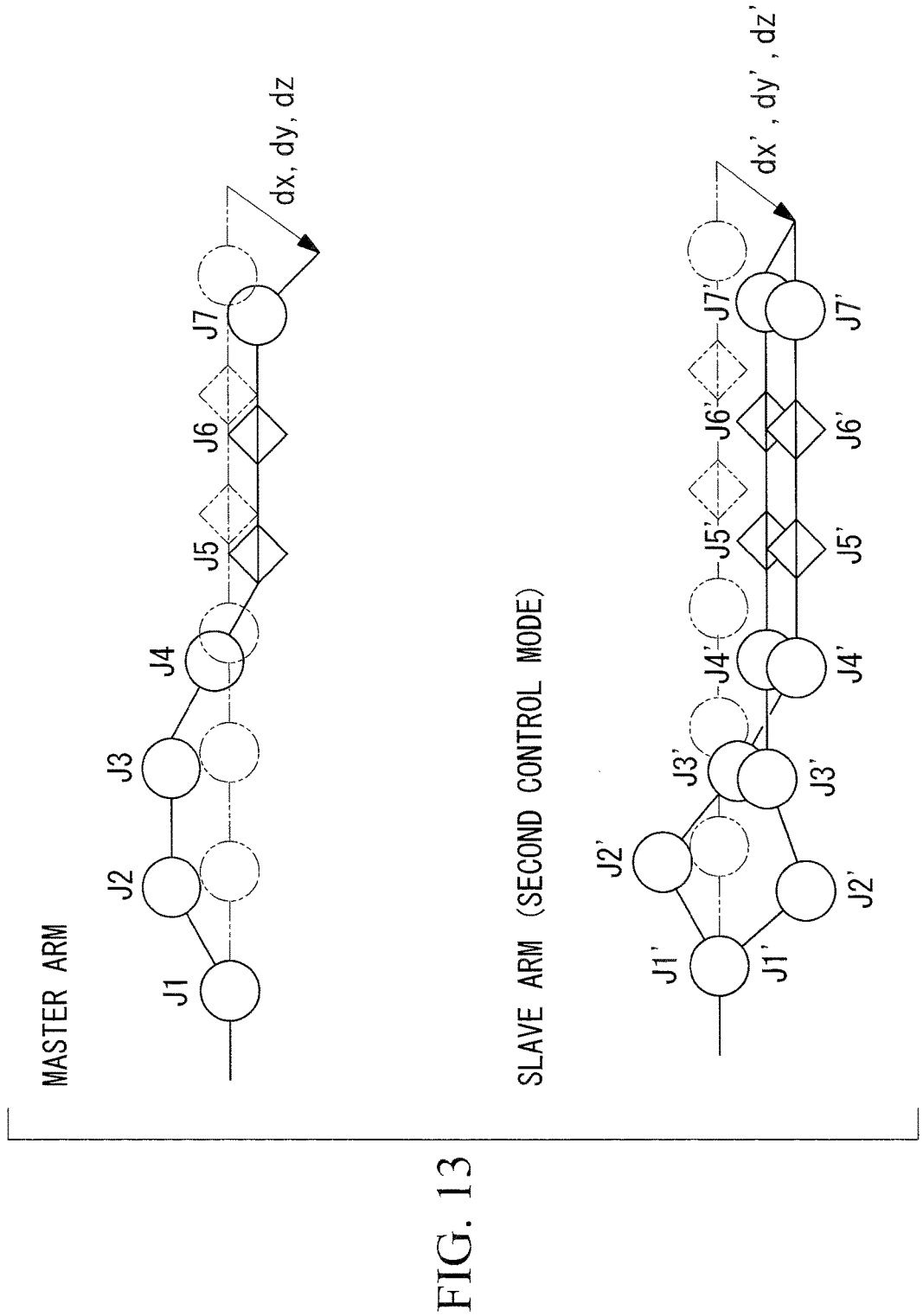
FIG. 13 is a diagram for explaining an operation in a second control mode of the slave arm in FIG. 11.

The "second control mode" is a mode that causes the distal end of the slave arm 6 to follow the motion of the distal end of the master arm 9. More specifically, as shown in FIG. 13, the control unit 3 uses the amount of change θi (i=1, 2, . . . , 7) in each joint Ji received from the operation input unit 2 to obtain the displacements dx', dy', dz' of the distal end of the slave arm 6 via a procedure similar to that in the first embodiment and by the use of these displacements dx', dy', dz', calculates the reverse kinematics of the slave arm 6. Here, if a plurality of solutions are obtained, the control unit 3 adopts the solution that minimizes the total of the amounts of rotation θi' (i=1, 2, . . . , 7) of the joints Ji', namely, the solution that minimizes the amount of the overall motion of the slave arm 6.

The operation of the medical system 200 with this structure will now be described with reference to FIGS. 14 and 15.

In this embodiment, the procedure up to positioning of the treatment part 8 close to the affected area is the same as in the first embodiment, except that the "first control mode" is selected by the control-mode manual change unit 12 (YES in step S1').

Figure 14:
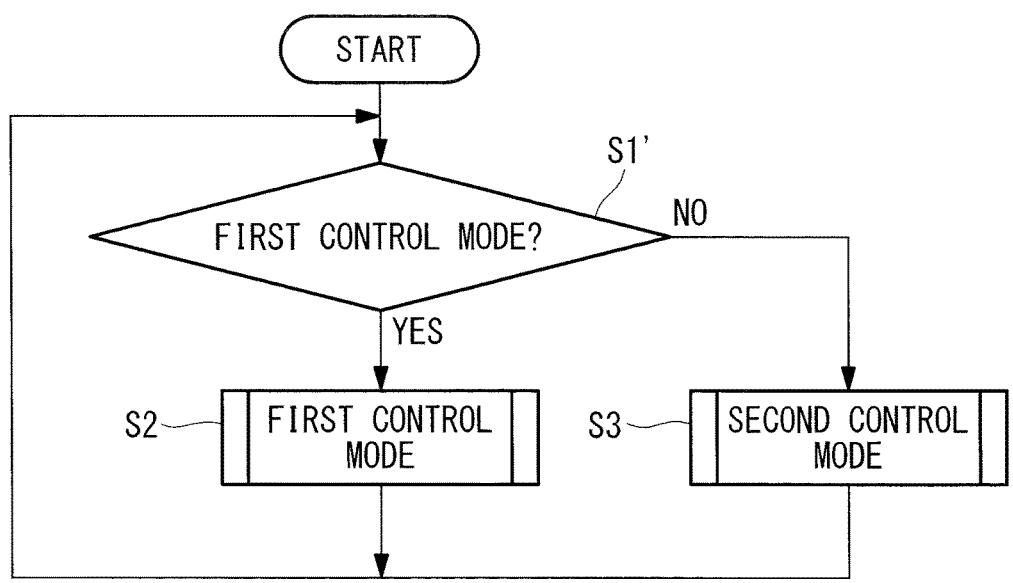
FIG. 14 is a flowchart illustrating a method for controlling a manipulator with a control unit of the medical system in FIG. 10.
Figure 15:
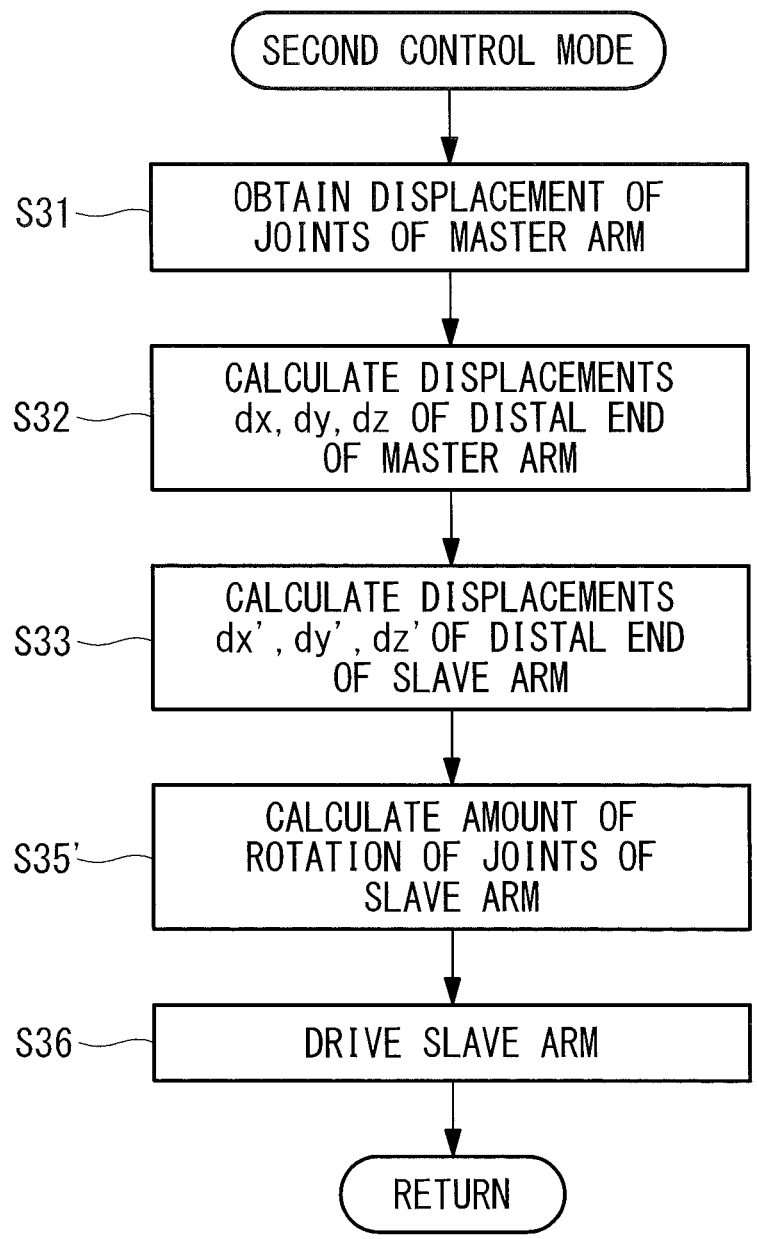
FIG. 15 is a flowchart illustrating a routine for the second control mode in FIG. 14.

As shown in FIG. 14, after positioning the treatment part 8 close to the affected area, the operator Op switches the "first control mode" to the "second control mode" with the control-mode manual change unit 12 (NO in step S1'). As shown in FIG. 15, in the "second control mode" of this embodiment, the slave arm 6 is controlled (step S36) so that the distal end of the slave arm 6 accurately follows the motion of the distal end of the master arm 9 (steps S33, S35') on the basis of movement of the distal end of the master arm 9 (steps S31, S32). At this time, however, the amount of overall motion of the slave arm 6 is suppressed to a minimum (step S35'). Therefore, the operator Op can focus attention only on the operation of the distal end of the slave arm 6 without having to pay attention to the overall shape of the slave arm 6.

In this manner, this embodiment affords an advantage in that the entire slave arm 6 is moved normally in a situation requiring a large motion of the slave arm 6, whereas motions of parts other than the distal end of the slave arm 6 are restricted in a situation requiring a minute motion, so that the slave arm 6 can be operated under an operating condition appropriate for each of the situations, thereby enhancing usability.

Also in this embodiment, it is preferable to perform the reset flow in the same manner as in the first embodiment when the control unit 3 is to switch the "second control mode" to the "first control mode."

Furthermore, in this embodiment, the motion-scale-ratio change unit 11 described in the first embodiment may also be provided. In this case, for calculating the reverse kinematics in the "second control mode," it is sufficient to use displacements kdx', kdy', kdz' instead of the displacements dx', dy', dz'. Alternatively, the control unit 3 may retain a predetermined motion scale ratio k to minutely move the distal end of the slave arm 6 at all times in the "second control mode."

In this embodiment, reverse kinematics in the "second control mode" are calculated with reference only to the position of the distal end of the slave arm 6. Instead of this, the positions and the orientations of some joints at the distal end of the slave arm 6 may be used as a reference.

More specifically, a constraint condition may be attached such that an arbitrary number of joints from the distal end of the slave arm 6 take a shape similar to that of the master arm 9, and the reverse kinematics may be calculated so that displacements in the positions and the orientations of the corresponding joints of the master arm 9 are followed.

In this case, a constraint condition like that described above may be attached to all joints J1' to J7' to geometrically calculate the reverse kinematics according to the displacement of the distal end of the master arm 9.

Alternatively, reverse kinematics of the slave arm 6 may be calculated according to the displacement in the position and orientation of the distal end of the master arm 9, and thereafter, the slave arm 6 may be moved so that any number of joints at the distal end of the slave arm 6 match the motion of the corresponding joints of the master arm 9. If the distal end has undesirably moved when the orientations of the joints were matched, the position thereof is restored to the original position by calculating the reverse kinematics once again. By repeating these operations for calculating displacements, in response to the entered instruction value, in the position and orientation of the distal end of the slave arm 6 until convergence is reached, reverse kinematics can be calculated with the constraint condition applied.

In this embodiment, the operator Op manually switches between the "first control mode" and the "second control mode." Instead of or in addition to this, the control unit (control-mode automatic change unit) 3 may automatically switch between the "first control mode" and the "second control mode" depending on the condition, circumstance, or environment in which the slave arm 6 is used.

The condition of use etc. of the slave arm 6 includes, for example, the type of the slave arm 6, whether or not the movement speed of a joint of the slave arm 6 is within a predetermined threshold, and whether or not the amount of displacement in a joint of the slave arm 6 is within a predetermined threshold.

For example, in FIG. 1, when the slave arm 6 is connected to the control unit 3, the control unit 3 reads out a memory chip provided in the slave arm 6 to recognize the type of the slave arm 6 (e.g., the treatment part 8 as a gripping forceps). The control unit 3 can acquire the control mode corresponding to the recognized type on the basis of pre-stored table information about types of the slave arm 6 and control modes to switch to an appropriate control mode.

Figure 16:
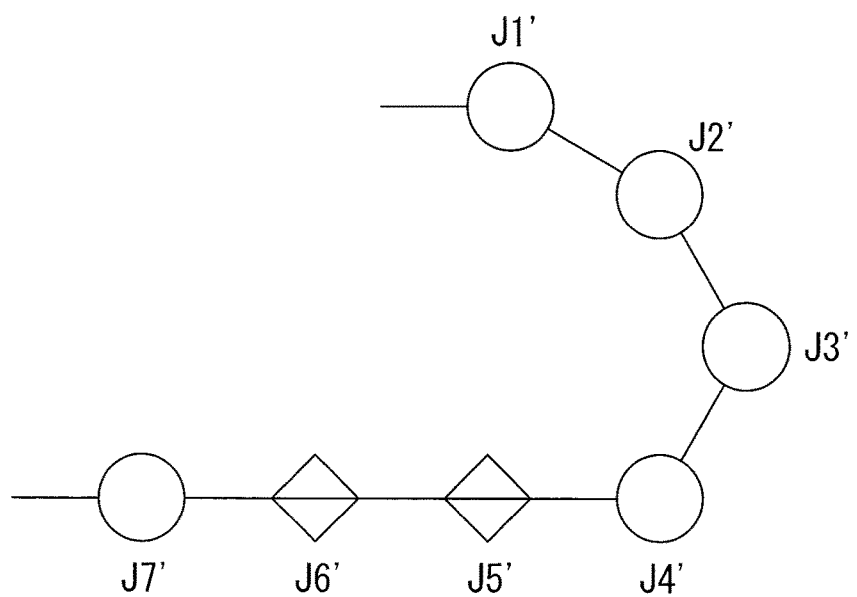
FIG. 16 is a diagram for explaining a modification of a method for switching the control mode.

For example, when a U-turn motion for reconfiguring the slave arm 6 into a U-shape is to be performed, as shown in FIG. 16, this motion may be followed by forcible selection of the "second control mode" by the control unit 3.

Furthermore, the control unit 3 determines whether or not the region reached by the distal end section of the slave arm 6 is a narrow space, and if this region is a narrow space on the basis of the result of determination, may forcibly select the "second control mode." Whether the space in which the distal end section of the slave arm 6 is positioned is large or small is determined by using, for example, image analysis of video images captured by the endoscope 5.

In addition, the control unit 3 may switch the control mode according to the type of the slave arm 6 associated with the master arm 9. For example, the control unit 3 may select the "first control mode" if the slave arm 6 is a retractor surgical instrument used for the purpose of a large motion such as traction or may select the "second control mode" if the slave arm 6 is a surgical energy device used mainly for the purpose of precise operations.

Furthermore, the control unit 3 may recognize the surgical situation on the basis of information including images, the surgical instrument employed, the operative technique, elapsed time, and the circumstances of the operating theater, thereby switching to the most appropriate control mode.

Alternatively, the control unit 3 may determine whether coarse-motion operation of the entire slave arm 6 or minute-motion operation of the distal end of the slave arm 6 is performed by the operator Op on the basis of the amount of change $\theta i$ in each joint $J i$ of the master arm 9, thereby switching between the "first control mode" and the "second control mode" on the basis of the determination result.

Or alternatively, when one of the rotational angles of the joints $J i$ has reached the maximum angle during control in the "first control mode," the control unit 3 may switch to the "second control mode."

From the above-described embodiments and modifications thereof, the following aspects of the invention are derived.

A first aspect of the present invention is a medical system including: a multi-joint slave arm; a master arm that has a joint structure structurally similar to the slave arm and is operated by an operator; and a control unit that controls the slave arm on the basis of an operation applied to the master arm, wherein the control unit can switch between a first control mode for controlling a rotational motion of each joint of the slave arm on the basis of an amount of rotation of each joint of the master arm so that the slave arm takes a shape similar to the master arm and a second control mode for controlling the rotational motion of each joint of the slave arm on the basis of a displacement of a predetermined region of a distal end section of the master arm so that a predetermined region of a distal end section of the slave arm follows a movement of the predetermined region of the distal end section of the master arm.

According to the first aspect of the present invention, because the slave arm and the master arm are similar to each other in the joint structure, the slave arm can be intuitively operated using the master arm.

In this case, the control unit causes the entire slave arm to follow the overall motion of the master arm in the first control mode. Therefore, the first control mode is suitable for coarse operation in which the slave arm is moved by a comparatively great amount. In contrast, in the second control mode, the control unit causes the predetermined region at the distal end section of the slave arm to follow the motion of the predetermined region at the distal end section of the master arm. Therefore, the second control mode is suitable for an intricate operation in which the predetermined region at the distal end section of the slave arm is accurately operated. In this manner, both coarse operation and intricate operation can be satisfied to enhance usability.

In the above-described first aspect, the control unit may control the slave arm so as to minimize an amount of change in a shape of the slave arm in the second control mode.

By doing so, because the amount of overall motion of the slave arm is suppressed to a minimum, the operator can further focus attention on the operation of the predetermined region at the distal end section of the slave arm.

Furthermore, in the above-described first aspect, the slave arm may be controlled so as to minimize the motion of a pre-registered particular joint (e.g., a joint highly likely to interfere with tissues due to its structure).

In the above-described first aspect, the control unit may control a rotational motion of any number of joints starting from a distal end of the slave arm so that these joints take a shape similar to the master arm in the second control mode.

By doing so, the distal end section of the slave arm can be operated more intuitively.

In the above-described first aspect, a ratio of an amount of motion of the slave arm to an amount of operation applied to the master arm may be a predetermined constant value in the first control mode and may be smaller than the predetermined constant value in the second control mode.

By doing so, the amount of motion of the slave arm in the second control mode becomes smaller than that in the first control mode. Because of this, the second control mode can be made even more suitable for an intricate operation.

In the above-described first aspect, a ratio of an amount of motion of the slave arm to an amount of operation applied to the master arm may be a predetermined constant value in the first control mode and may be smaller than the predetermined constant value in the second control mode, and in the second control mode, the control unit may calculate reverse kinematics of the slave arm on the basis of a position of the predetermined region of the distal end section of the master arm and may select, from among an obtained plurality of solutions, a solution that causes the shape of the slave arm to be closest to the shape of the master arm.

By doing so, not only can the second control mode be made more suitable for intricate operation, but also the shape and the orientation of the slave arm can be coarsely recognized on the basis of the master arm.

In the above-described first aspect, the control unit may select a solution that minimizes a total of differences between an amount of displacement of each joint of the master arm and an amount of displacement of each joint of the slave arm in the second control mode.

Furthermore, in the above-described first aspect, if four spaces defined by two planes that pass through a central axis of a basal part of each of the slave arm and the master arm and that are orthogonal to each other on the central axis are assumed, the control unit may select a solution that causes the slave arm to be positioned in a space corresponding to a space in which the master arm is positioned.

By doing so, a solution that causes the shape and the orientation of the slave arm to approximate to the shape and the orientation of the master arm can be selected via a simple calculation.

In the above-described first aspect, in the second control mode, the control unit may control the slave arm so as to place a most distal joint of the slave arm at a position and an orientation corresponding to a position and an orientation of a most distal joint of the master arm.

The above-described first aspect may include a motion-ratio change unit that changes the ratio of the amount of motion to the amount of operation.

By doing so, the ratio can be changed to an appropriate value, as required, to further enhance usability.

The above-described first aspect may include a control-mode manual change unit that allows the operator to select one of the first control mode and the second control mode.

By doing so, the operator can switch the control mode with an arbitrary timing. The control-mode manual change unit may be an input device like a switch.

The above-described first aspect may include a control-mode automatic change unit that switches the control mode depending on a condition, circumstance, or environment of use of the slave arm.

By doing so, it is possible to automatically switch to an appropriate control mode with an appropriate timing.

In the above-described first aspect, the control-mode automatic change unit may switch between the first control mode and the second control mode depending on a type of the slave arm.

By doing so, it is possible to automatically switch to a control mode suitable for the application of individual slave arms.

In the above-described first aspect, when switching from the second control mode to the first control mode, the control unit may perform a reset flow for moving at least one of the master arm and the slave arm before the first control mode is started so as to match the amounts of displacements of individual joints of the master arm and the slave arm.

By doing so, the first control mode can be smoothly started in a state where the overall positions and orientations of the master arm and the slave arm are matched.

A second aspect of the present invention is a method for controlling a medical system including a multi-joint slave arm and a master arm that has a joint structure structurally similar to the slave arm and that is operated by an operator, wherein a control mode for controlling the slave arm can be switched between a first control mode for controlling a rotational motion of each joint of the slave arm on the basis of an amount of rotation of each joint of the master arm so that the slave arm takes a shape similar to the master arm and a second control mode for controlling a rotational motion of each joint of the slave arm on the basis of a displacement of a predetermined region of a distal end section of the master arm so that a predetermined region of a distal end section of the slave arm follows a movement of the predetermined region of the distal end section of the master arm.

REFERENCE SIGNS LIST

1 Manipulator
2 Operation input unit
3 Control unit (control-mode automatic change unit)
4 flexible part
5 Endoscope
6 Slave arm
8 Distal treatment part
9 Master arm
10 Display unit
11 Motion-scale-ratio change unit (motion-ratio change unit)
12 Control-mode manual change unit
100, 200 Medical system
J1 to J7, J1' to J7' Joint
Op Operator
P Patient

The invention claimed is:

1. A medical system comprising:
a multi-joint slave arm;
a master arm that has a joint structure structurally similar to the multi-joint slave arm and is operated by an operator; and
a controller that controls the multi-joint slave arm on the basis of an operation applied to the master arm,
wherein the controller is configured to switch between a first control mode for controlling a rotational motion of each joint of the multi-joint slave arm on the basis of an amount of rotation of each joint of the master arm so that the multi-joint slave arm takes a shape similar to the master arm and a second control mode for controlling the rotational motion of each joint of the multi-joint slave arm on the basis of a displacement of a predetermined region of a distal end section of the master arm so that a predetermined region of a distal end section of the multi-joint slave arm follows a movement of the predetermined region of the distal end section of the master arm; and
a ratio of an amount of motion of the multi-joint slave arm to an amount of operation applied to the master arm is a predetermined constant value in the first control mode and is smaller than the predetermined constant value in the second control mode.

2. The medical system according to claim 1, wherein the controller is further configured to control the multi-joint slave arm so as to minimize an amount of change in a shape of the multi-joint slave arm in the second control mode.

3. The medical system according to claim 1, wherein the controller is further configured to control a rotational motion of any number of joints starting from a distal end of the multi-joint slave arm so that said joints take a shape similar to the master arm in the second control mode.

4. The medical system according to claim 1, wherein
in the second control mode, the controller is configured to calculate reverse kinematics of the multi-joint slave arm on the basis of a position of the predetermined region of the distal end section of the master arm and select, from among an obtained plurality of solutions, a solution that causes the shape of the multi-joint slave arm to be closest to the shape of the master arm.

5. The medical system according to claim 4, wherein the controller is configured to select a solution that minimizes a total of differences between an amount of displacement of each joint of the master arm and an amount of displacement of each joint of the multi-joint slave arm in the second control mode.

6. The medical system according to claim 5, wherein the controller is configured to change the ratio of the amount of motion to the amount of operation.

7. The medical system according to claim 4, wherein if four spaces defined by two planes that pass through a central axis of a basal part of each of the multi-joint slave arm and the master arm and that are orthogonal to each other on the central axis are assumed, the controller is configured to select a solution that causes the multi-joint slave arm to be positioned in a space corresponding to a space in which the master arm is positioned.

8. The medical system according to claim 7, wherein the controller is configured to change the ratio of the amount of motion to the amount of operation.

9. The medical system according to claim 4, wherein in the second control mode, the controller is configured to control the multi-joint slave arm so as to place a most distal joint of the multi-joint slave arm at a position and an orientation corresponding to a position and an orientation of a most distal joint of the master arm.

10. The medical system according to claim 1, wherein the controller is configured to change the ratio of the amount of motion to the amount of operation.

11. The medical system according to claim 1, wherein the controller is configured to receive an instruction from the operator to select one of the first control mode and the second control mode.

12. The medical system according to claim 1, wherein the controller is configured to switch between the first control mode and the second control mode depending on a condition, circumstance, or environment of use of the multi-joint slave arm.

13. The medical system according to claim 12, wherein the controller is configured to switch between the first control mode and the second control mode depending on a type of the multi-joint slave arm.

14. The medical system according to claim 1, wherein when switching from the second control mode to the first control mode, the controller is configured to perform a reset flow for moving at least one of the master arm and the multi-joint slave arm before the first control mode is started so as to match the amounts of displacements of individual joints of the master arm and the multi-joint slave arm.

15. A method for controlling a medical system including a multi-joint slave arm and a master arm that has a joint structure structurally similar to the multi-joint slave arm and that is operated by an operator,
wherein a control mode for controlling the multi-joint slave arm can be switched between a first control mode for controlling a rotational motion of each joint of the multi-joint slave arm on the basis of an amount of rotation of each joint of the master arm so that the multi-joint slave arm takes a shape similar to the master arm and a second control mode for controlling a rotational motion of each joint of multi-joint slave arm on the basis of a displacement of a predetermined region of a distal end section of the master arm so that a predetermined region of a distal end section of the multi-joint slave arm follows a movement of the predetermined region of the distal end section of the master arm; and
a ratio of an amount of motion of the multi-joint slave arm to an amount of operation applied to the master arm is a predetermined constant value in the first control mode and is smaller than the predetermined constant value in the second control mode.

16. A medical system comprising:
a multi-joint slave arm;
a master arm that has a joint structure structurally similar to the multi-joint slave arm and is operated by an operator; and
a controller configured to control the multi-joint slave arm on the basis of an operation applied to the master arm,
wherein the controller is configured to switch between a first control mode for controlling a rotational motion of each joint of the multi-joint slave arm on the basis of an amount of rotation of each joint of the master arm so that the multi-joint slave arm takes a shape similar to the master arm and a second control mode for controlling the rotational motion of each joint of the multi-joint slave arm on the basis of a displacement of a predetermined region of a distal end section of the master arm so that a predetermined region of a distal end section of the multi-joint slave arm follows a movement of the predetermined region of the distal end section of the master arm; and
the controller controls the multi-joint slave arm so as to minimize an amount of change in a shape of the multi-joint slave arm in the second control mode.

17. The medical system according to claim 16, wherein the controller is configured to control a rotational motion of any number of joints starting from a distal end of the multi-joint slave arm so that said joints take a shape similar to the master arm in the second control mode.

18. The medical system according to claim 16, wherein a ratio of an amount of motion of the multi-joint slave arm to an amount of operation applied to the master arm is a predetermined constant value in the first control mode and is smaller than the predetermined constant value in the second control mode, and
in the second control mode, the controller is configured to calculate reverse kinematics of the multi-joint slave arm on the basis of a position of the predetermined region of the distal end section of the master arm and select, from among an obtained plurality of solutions, a solution that causes the shape of the multi-joint slave arm to be closest to the shape of the master arm.

19. The medical system according to claim 16, wherein the controller is configured to receive an instruction from the operator to select one of the first control mode and the second control mode.

20. The medical system according to claim 16, wherein the controller is configured to switch between the first control mode and the second control mode depending on a condition, circumstance, or environment of use of the multi-joint slave arm.

21. The medical system according to claim 16, wherein when switching from the second control mode to the first control mode, the controller is configured to perform a reset flow for moving at least one of the master arm and the multi-joint slave arm before the first control mode is started so as to match the amounts of displacements of individual joints of the master arm and the multi-joint slave arm.

* * * * *